United States Patent [19]

Tsuchiya et al.

[11] 4,122,840
[45] Oct. 31, 1978

[54] APPARATUS FOR ANALYZING THE BALANCING FUNCTION OF THE HUMAN BODY

[75] Inventors: Kazuo Tsuchiya, Nagoya; Noboru Ohnishi, Okazaki, both of Japan

[73] Assignee: Yaesu Rehabili Co., Ltd., Tokyo, Japan

[21] Appl. No.: 799,690

[22] Filed: May 23, 1977

[30] Foreign Application Priority Data

Jun. 1, 1976 [JP] Japan .................................. 51-63879

[51] Int. Cl.² ............................................. A61B 5/10
[52] U.S. Cl. .................................. 128/2 S; 35/22 R; 340/573; 340/666
[58] Field of Search ............... 128/2 R, 2 S; 35/22 R; 340/272, 279, 282

[56] References Cited

U.S. PATENT DOCUMENTS

| | | | |
|---|---|---|---|
| 2,043,187 | 6/1936 | Owens | 128/2 S |
| 2,095,268 | 10/1937 | Roberts | 128/2 S |
| 3,420,222 | 1/1969 | Noe et al. | 128/2 S |
| 3,781,843 | 12/1973 | Harrison | 340/272 |
| 3,850,034 | 11/1974 | Tsuchiya et al. | 128/2 S |
| 3,906,931 | 9/1975 | Terekhov | 128/2 S |
| 4,014,398 | 3/1977 | Gresko | 128/2 S |

*Primary Examiner*—William E. Kamm
*Attorney, Agent, or Firm*—Haseltine, Lake, & Waters

[57] ABSTRACT

A person to be tested steps on a pair of foot steps, and a plurality of body load detectors sense the body load of the person, as applied to the foot steps. An arithmetic circuit receives the body load signals and provides difference signals which are displayed so that the person being tested can observe them. The person being tested sees body load distribution patterns on the display, and adjusts his body balance as a function thereof. Maximum-length linear shift register signals are provided which unbalance the body load distribution of the person being tested while standing on the foot steps. When the person observes these signals in the form of target signals, that person attempts to adjust the body load distribution so as to result in a balanced condition.

11 Claims, 9 Drawing Figures

APPARATUS FOR ANALYZING THE BALANCING FUNCTION OF THE HUMAN BODY

BACKGROUND OF THE INVENTION

The present invention for analyzing the human body's balancing function is employable in the medical fields. In particular it is adapted to quantitatively analyze with high accuracy the balancing function of the physically handicapped who have lost the body's normal balancing function and evaluate the results.

The human body's balancing function is indispensable for human beings leading social lives. In case the lower or upper limbs of a human being have been lost by accident or disease, artificial limbs or the like are provided in place of them, and thereafter proper rehabilitation trainings are effected in an endeavour to adjust or recover the body's balancing function. However, the adjusting and recovering means to be thus applied onto the physically handicapped have been either by means of the doctor's or any other curative's naked observations, or by means of the physically handicapped's subjective judgements. As a consequence, the present status in this medical field is that sufficiently proper and quantitative rehabilitation training of the physically handicapped has been impossible.

SUMMARY OF THE INVENTION

Accordingly, it is an object of the present invention to provide an apparatus for analyzing the human body's balancing function which is adapted to analyze the body load distributions of the person tested and display the analyzed results so as to enable the person tested to autonomously sense his balancing adjustability by means of visual feedbacks and obtain his own proper balancing ability.

It is another object of the present invention to provide an apparatus, for analyzing the human body's balancing function, which is adapted to heteronymously disturb the balanced conditions of the person tested into an unbalanced one and make the person tested autonomously correct the unbalanced condition into a balanced one, and learn the feeling of this correction.

It is another object of the present invention to provide apparatus for analyzing the human body's balancing function, which is able to analyze the human body's balancing function and evaluate the thus analyzed results with a high degree of accuracy that the prior art could not achieve.

The novel features which are considered as characteristic for the invention as set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE INVENTION

Figure 1:
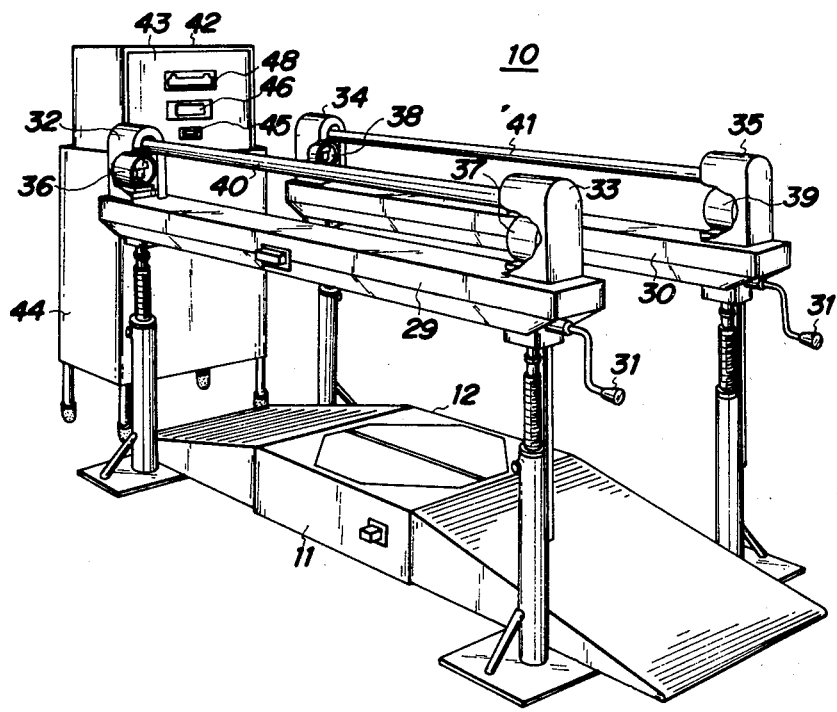
FIG. 1 is a perspective view, partially cut away, showing an example of an apparatus for analyzing the human body's balancing function according to the present invention.
Figure 4:
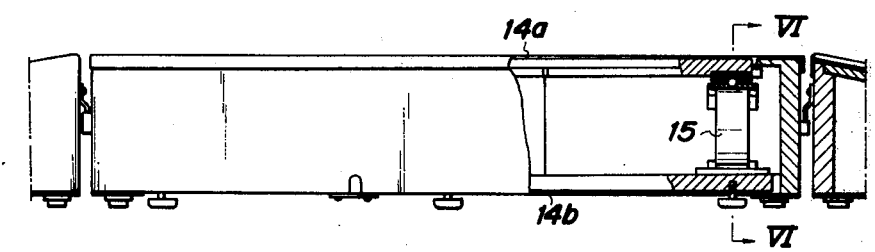
FIG. 4 is an enlarged partially cut away side view of the foot steps of the apparatus shown in FIG. 1.
Figure 2:
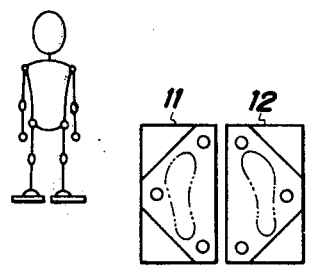
FIGS. 2 and 3 are diagrammatic views showing the way in which a person tested gets on the foot steps of the apparatus shown in FIG. 1.
Figure 3:
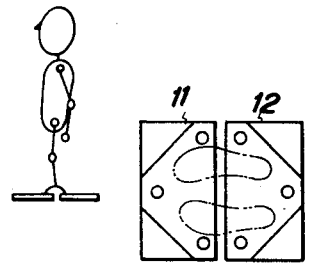

Referring to the drawings, in FIG. 1, there is shown apparatus for analyzing the human body's balancing function 10. A pair of foot steps 11, 12, are provided, parallel with each other and keeping a proper distance between them. The person being tested puts his right and left feet on them via a sloped auxiliary foot step are provided in case the body load distribution in the right and left directions of the person tested is to be analyzed, the person tested gets on the foot steps 11 and 12 as shown in FIG. 2. On the other hand, in case the body load distribution in the forward and backward directions of the person tested is to be analyzed, the person tested gets on the foot steps 11 and 12 as shown in FIG. 3.

Figure 6:
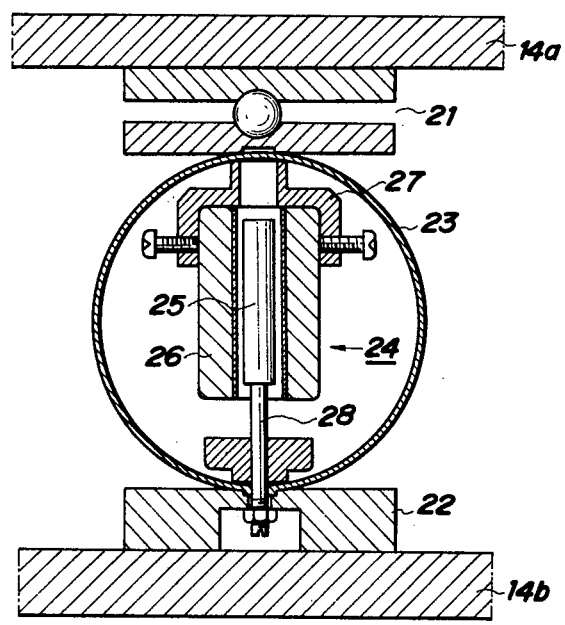
FIG. 6 is an enlarged cross-sectional view taken on line VI — VI of FIG 4.

Between the top plate 14a and bottom plate 14b of each of the foot steps 11 and 12 are vertically disposed body load detectors 15,16,17 and 18,19,20 each of which consists of a differential transformer as shown in FIG. 6. And, between the upper support member 21 beneath the top plate 14a and the lower support member 22 above the bottom plate 14b is interposed a spring plate 23 bent round, within which a differential transformer 24 consisting of a core 25 and a coiled sensor 26 is provided. The coiled senser 26 is fixed to the upper support member 21 via a stand 27, while the lower end of a support rod 28, which supports the core 25, is fixed onto the lower support member 22. When any load is applied onto the top plate 14a, the coiled senser 26 lowers against the expansional spring force of the spring plate 23 bent around. As a result an electrical signal corresponding to this differential movement with respect to the fixed core 25 develops from the differential transformer 24. A piezoelectric element that directly convert the applied pressure into an electrical signal or a strain gauge may be used instead of the differential transformer 24.

Referring back to FIG. 1, a pair of beams 29,30, whose heights are adjustable by the adjust handle 31, are provided side by side with the foot steps 11 and 12. Upon each end of the parallel beams 29,30 are provided cover members 32,33,34 and 35 within which body load detectors 36,37,38 and 39 are provided. Each of these body load detectors 36,37,38 and 39 has the same constitution as that of the body load detectors 15,16,17 and 18, 19,20 within the foot steps 11 and 12 — as explained in detail with reference to FIG. 6. Being supported respectively at each end by the body load detectors 36,37 and 38,39, a pair of transverse bars 40,41 are provided in parallel with each other so that the person tested who gets on the foot steps 11 and 12 may hold them by his hands and thus assist the body balance maintenance force in case he is unable to stand on his feet. The assisting force for the body balance maintenance thus applied onto the transverse bars 40,41 via the arms of the person tested are detected by the body load detectors 36,37,38 and 39.

Figure 7:
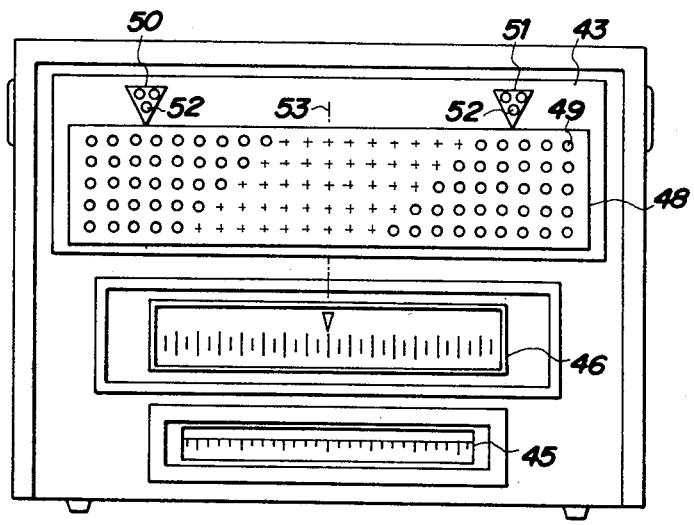
FIG. 7 is an enlarged view of the display panel of the control box as shown in FIG. 1.

At a location where the person tested is able to set it, is a control box 42 whose display panel 43 is put on a cabinet 44. As shown enlarged in FIG. 7, the meter 45 provided on the display panel 43 is to indicate the body load distribution trend and distribution difference of the person tested applied onto the transverse bars 40,41 in case the person tested gets on the foot steps 11 and 12 by grasping the bars 40,41 with his hands so as to assist the body balance maintenance. The meter 46 provided on the display panel 43 is to indicate the body load distribution trend and distribution difference of the person tested applied onto the foot steps 11 and 12.

The reference numeral 48 designates a display which consists of a plurality of luminous diodes 49 provided in matrix arrangements. Above the display 48, a pair of symmetric target signal displays 50,51 are provided, each of these consists of a plurality of luminous diodes 52. The body load distribution of the person tested, who reacts in view of the target signals on the target signal display 50,51, that are put on and off alternately as mentioned hereinafter, is indicated by transfers of bright lines of the luminous diodes 49 in varying rows with respect to a bright line of the luminous diodes 49 in a reference row 53.

Figure 8:
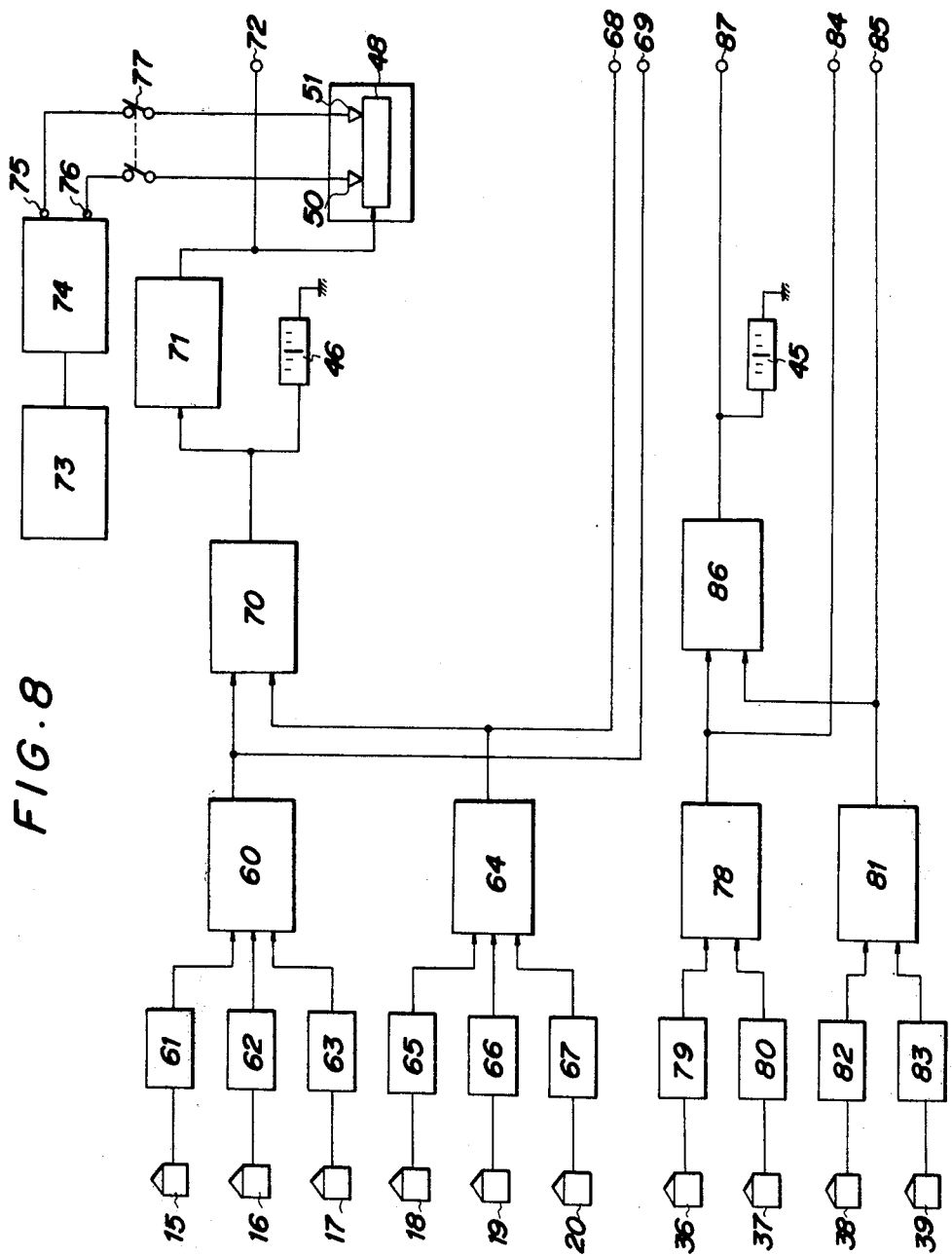
FIG. 8 is a block diagram showing an example of the analytical arithmetic circuit employed in the present invention.

Within the control box 42 is stored an analytical arithmetic circuit which receives body load signals detected by the body load detectors 15,16,17 and 18,19,20 provided within the foot steps 11 and 12 and/or the body load detectors 36,37 provided beneath the ends of the transverse bars 40 and the body load detectors 38,39 provided beneath the ends of the transverse bar 41. It analytically operates and displays the same on the display panel 43. One example of this analytical arithmetic circuit will be explained now, referring to the block diagram shown in FIG. 8.

Body load signals detected by the body load detectors 15,16,17 provided within the foot step 11 are added together at an adder 60 after having been converted into D.C. signals through rectifiers 61,62,63. Likewise, body load signals detected by the body load detectors 18,19,20 provided within the foot step 12 are added together at an adder 64 after having been converted into D.C. signals through rectifiers 65,66,67. Output signals of the adders 60,64 are sent via terminals 68,69 to a recorder (not shown) and recorded there as the signals indicating the body load distributions of the person tested on the right and on the left. On the other hand, the output signals of the adder 60,64 are applied onto a subtractor 70 which effects a subtraction of the two signals thus applied, and provides an output difference signal corresponding to the difference of body load distribution on the right and on the left of the person tested. The difference output signal of the subtractor 70 is supplied to the meter 46 provided on the display panel 43 which indicates the body load distribution trend and distribution difference of the person tested applied onto the foot steps 11 and 12. Further, after having been suitably amplified via an amplifier 71, the difference output signal of the subtractor 70 is supplied to the luminous diodes 49 constituting the display 48 whereupon the body load distribution trend and difference of the person tested are displayed as the luminous zone of the luminous diodes 49 between the reference row 52 and another row. The difference signal from the amplifier 71 is sent to the recorder (not shown) via a terminal 72 and recorded as the body load distribution difference on the right and left of the person tested.

Figure 9:
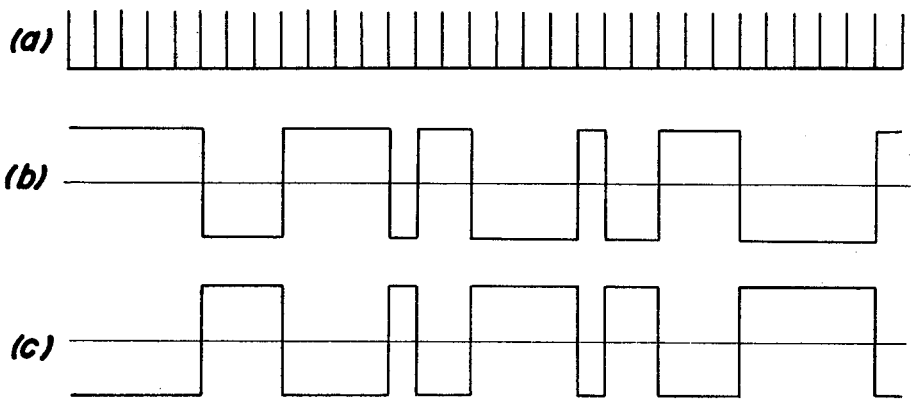
FIG. 9(a), (b) and (c) are wave form charts employed in the circuit of FIG. 8.
Figure 5:
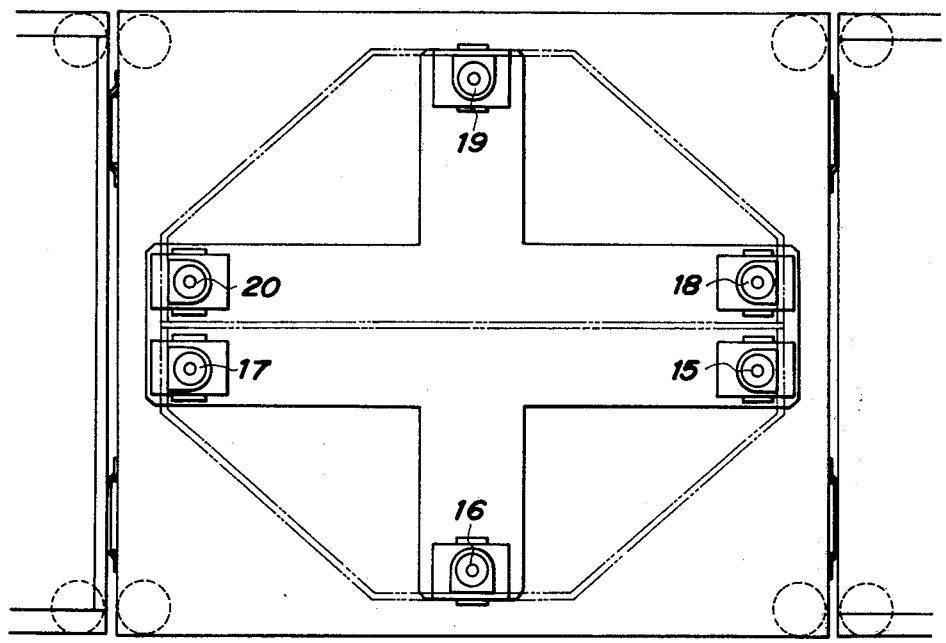
FIG. 5 is a top plan view, with the top plate taken away, of FIG. 4.

The clock pulse generator 73 provides a signal consisting of a clock pulse train of a constant period as shown in FIG. 9(a) and supplies the same to a maximum-length linear shift register signal generator 74, which develops, from a terminal 75, a maximum-length linear shift register signal as shown in FIG. 9(b) and from another terminal 76 another maximum-length linear shift register signal which is complementary to that from the terminal 75 as shown in FIG. 9(c). The maximum-length linear shift register signals from the terminals 75 and 76 are of the width of integer multiples of the clock pulse trains from the clock pulse generator 73, and are pseudo-random to such an extent as to exclude the probability of a human being anticipating them.

The maximum-length linear shift register signals from the terminals 75 and 76 are respectively supplied to the luminous diodes 52 constituting the target signal display 50,51 which are adapted to be put on and off alternately upon receipt of the maximum-length linear shift register signals. When the target signal display 50,51 are not desired to be energized, the apparatus will be used with the switch 77 set to off position.

Body load distribution signals detected by the body load detectors 36,37 are added together at an adder 78 after having been converted into D.C. signals through rectifiers 79,80. Likewise, body load signals detected by the body load detectors 39,39 are added together at an adder 81 after having been converted into D.C. signals through rectifiers 82,83. Output signals of the adders 78,81 are sent via terminals 84,85 to the recorder (not shown) and recorded there as the signals indicating the body load distributions of the person tested applied onto the transverse bars 40 and 41 respectively via his arms. On the other hand, the output signals of the adders 78,81 are applied onto a subtractor 86 which effects a subtraction of the two signals thus applied, and provides a difference signal corresponding to the difference of body load distribution applied onto the transverse bars 40 and 41 via the arms of the person tested. The difference output signal of the subtractor 86 is supplied to the meter 45 on the display panel 43 which indicates the body load distribution trend and distribution difference of the person tested applied onto the transverse bars 40,41 in case the person tested gets on the foot steps 11 and 12 by holding the transverse bars 40,41 with his hands so as to assist the body load maintenance. And, the difference output signals of the subtractor 86 is sent to the recorder (not shown) via a terminal 87 and recorded there.

In the operation of the apparatus for analyzing the human body's balancing function with the switch 77 set to off position so as not to energize the luminous diodes 52 constituting the target signal display 50,51, the person tested gets on the foot steps 11 and 12 and tries to autonomously adjust his body balance so as to keep at zero each needle of the meter 45,46 provided on the display panel 43. He is kept informed of his body balance distributions at any transitional time by the luminous zones of luminous diodes 49 constituting the display 48. This adjustment operation of the body balance of the person tested by the apparatus of this invention is effective when applied to the following case (1), (2) and (3):

(1) The training of body load limitations onto affected portions of a patient who has broken bones;

(2) The indication of an unbalanced quantity of body load support by the hands of a patient when either limb has been cut off or when the muscles are paralyzed and the training thereof;

(3) The indication of an unbalance of body load applied upon the right and left feet and the training to recover the balancing sensitivity.

On the other hand, in the operation of the apparatus of this invention with the switch 77 set to on so as to energize the luminous diodes 52 constituting the target signals display 50,51 by the maximum-length linear shift register signals and provide target signals to heteronymously unbalance the body load distributions of the person tested who gets on the foot steps 11 and 12, that person tries to autonomously recover the body load distributions. This operation of the apparatus of this invention is effective when applied to the paralyzed patient, or a patient of myotonic dystrophy or sufacute myelo-optico-neuropathy or Parkinson's disease or other diseases, in the following cases (4), (5) and (6) in addition to the cases (1), (2) and (3) mentioned above:

(4) Evaluation of the human body's load transition function of the motor center;

(5) The training of the human body's load transition function (both forward-backward and right-leftward load transition trainings are possible);

(6) The preparatory training of walking.

In these operations, it becomes possible, if the maximum-length linear shift register signals are assumed as inputs and the body load distribution signals of the person tested, indicated as the luminous zones of luminous diodes 49, are assumed as outputs, to quantitatively evaluate the transmission functions of the motor center control system of the person tested, by the autocorrelation coefficient of these inputs and outputs. Further, inasmuch as the maximum-length linear shift register signals, to be given as the target signals to heteronymously disturb the body balance of the person tested, are the ones which have excluded the probability of the anticipation function of the person tested as regards the regularity of the signals, the person tested is able to obtain a quite reliable sense for adjustments and corrections of his body balance.

Taking into account the data of the body load distributions of the person tested applied onto his right and left feet and arms and distribution difference as recorded in the recorder via the terminals 68,69,72,84,85,87, the apparatus for analyzing the human body's balancing function of this invention makes it possible to analyze and evaluate the human body's balancing function with higher accuracy than the prior art could achieve and provides the patient who has lost his balancing function with proper rehabilitation training.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalents of the following claims.

What is claimed is:

1. In an apparatus for analyzing human body's balancing function adapted to analyze the body load distributions of a person tested and applied onto his right and left feet so as to adjust his body balance, the improvement comprising: a pair of parallel foot steps spaced from each other, the person tested placing right and left feet on said foot steps; a plurality of body load detectors within said foot steps so as to detect body load distributions applied onto the right and left feet of the person tested;

an arithmetic circuit for receiving the body load signals detected by the plurality of body load detectors and developing a difference signal corresponding to the body load distributions applied onto the right and left feet of the person tested; and display means for displaying the difference signal from the arithmetic circuit and informing the person tested of the adjustability of his body balancing by visual feedbacks.

2. In an apparatus for analyzing a human body's balancing function as claimed in claim 1, the improvement further comprising:

a pair of transverse bars located side by side with said pair of foot steps so as to enable the person tested on the foot steps to hold them by his hands and thereby assist his body balance maintenance force;

a plurality of body load detectors beneath the ends of the transverse bars for detecting the body balance maintenance assistance force by the person tested applied onto the transverse bars;

an arithmetic circuit for receiving the body balance maintenance assistance force from the plurality of body load detectors and developing a difference signal corresponding to the body load distribution difference applied onto the transverse bars; and display means to display the last-mentioned difference signals.

3. In an apparatus for analyzing human body's balancing function as claimed in claim 2, wherein said arithmetic circuit comprises:

a first adder for adding the body load distribution signals detected by the body load detectors provided within one of the foot steps;

a second adder for adding the body load distribution signals detected by the body load detectors provided within the other of the foot steps; and a subtractor which effects a subtraction of the output signals from said first and second adders.

4. In an apparatus for analyzing human body's balancing function as claimed in claim 2, wherein each of said body load detectors within the foot steps and beneath the transverse bars comprises a differential transformer.

5. In an apparatus for analyzing human body's balancing function as claimed in claim 1, wherein said display means comprises a plurality of luminous diodes in matrix arrangements for showing the body load distributions of the person tested as luminous zones between bright lines of the luminous diodes in a reference row and another transferring row.

6. In an apparatus for analyzing a human body's balancing function by analyzing the body load distributions of a person tested and applied onto right and left feet so as to adjust the body balance, the improvement comprising;

a pair of parallel foot steps spaced from each other, the person tested placing right and left feet on said foot steps;

a plurality of body load detectors within said foot steps for detecting the body load distributions applied onto the right and left feet of the person tested;

an arithmetic circuit for receiving the body load distribution signals detected by said body load detectors and developing a difference signal of the body load distributions applied onto the right and left feet of the person tested;

a target signal generator providing target signals in the view of the person on the foot steps to render his balanced body load distribution into unbalanced condition;

target signal display means for receiving said target signals and displaying the same; and display means for displaying the difference signal from the arithmetic circuit and/or the transfers of the body load distributions of the person tested when reacting while viewing the target signals shown on the target signal display means.

7. In an apparatus for analyzing human body's balancing function as claimed in claim 6, the improvement further comprising;

a pair of transverse bars side by side with said pair of foot steps so as to enable a person tested on the foot steps to hold them by his hands and assist his body balance maintenance force;

a plurality of body load detectors beneath the ends of said transverse bars so as to detect the body balance maintenance assistance force by said person applied onto the transverse bars;

an arithmetic circuit for receiving the body balance maintenance assistance force from the plurality of body load detectors and developing a difference signal corresponding to the body load distribution difference applied onto said transverse bars; and display means for displaying the difference signals.

8. In an apparatus for analyzing a human body's balancing function as claimed in claim 7, wherein the arithmetic circuit comprises:

a first adder for adding body load distribution signals detected by the body load detectors provided within one of the foot steps;

a second adder for adding the body load distribution signals detected by the body load detectors provided within the other of said foot steps; and a substractor for subtraction of the output signals from the first and second adders.

9. In an apparatus for analyzing a human body's balancing function as claimed in claim 7, wherein each of the body load detectors within said foot steps and beneath the transverse bars comprises a differential transformer.

10. In an apparatus for analyzing human body's balancing function as claimed in claim 6, wherein said display means comprises a plurality of luminous diodes in matrix arrangements for showing the body load distributions of said person as luminous zones between bright lines of the luminous diodes in a reference row and another row.

11. In an apparatus for analyzing a human body's balancing function as claimed in claim 6, wherein said target signal generator comprises a clock pulse generator emitting clock pulse signals of constant period, and a maximum-length linear shift register signal generator for receiving the clock pulse signals from the clock pulse generator and developing maximum-length linear shift register signals as target signals for the person tested.

* * * * *